United States Patent [19]

Fahlstrom et al.

[11] Patent Number: 4,913,147
[45] Date of Patent: Apr. 3, 1990

[54] HEART PACEMAKER SYSTEM WITH SHAPE-MEMORY METAL COMPONENTS

[75] Inventors: Ulf Fahlstrom, Stockholm; Jakub Hirschberg, Taeby, both of Sweden

[73] Assignee: Siemens Aktiengesellschaft, Berlin and Munich, Fed. Rep. of Germany

[21] Appl. No.: 100,250

[22] Filed: Sep. 23, 1987

[30] Foreign Application Priority Data

Sep. 23, 1986 [DE] Fed. Rep. of Germany ....... 3632186

[51] Int. Cl.⁴ .............................................. A61N 1/36
[52] U.S. Cl. ................................. 128/419 P; 128/785; 128/786
[58] Field of Search .................. 128/419 P, 786, 785; 439/161

[56] References Cited

U.S. PATENT DOCUMENTS

| | | | |
|---|---|---|---|
| 3,416,534 | 10/1968 | Quinn | 128/419 P |
| 3,719,190 | 3/1973 | Avery | 128/419 P |
| 3,868,956 | 3/1975 | Alfidi et al. | 128/1 R |
| 3,890,977 | 6/1975 | Wilson | 128/418 |
| 3,902,501 | 9/1975 | Citron et al. | 128/419 P |
| 4,282,885 | 8/1981 | Bisping | 128/419 P |
| 4,473,715 | 9/1984 | Beinhaur et al. | 174/87 |
| 4,566,467 | 1/1986 | DeHaan | 128/784 |
| 4,717,352 | 1/1988 | De Mendez et al. | 439/161 |
| 4,722,353 | 2/1988 | Sluetz | 128/419 P |

FOREIGN PATENT DOCUMENTS

| | | | |
|---|---|---|---|
| 0167735 | 8/1986 | European Pat. Off. | |
| 1032034 | 3/1953 | France | |
| 2334218 | 4/1977 | France | |
| 0187667 | 8/1986 | Japan | 439/161 |

OTHER PUBLICATIONS

"What you can do with that 'memory' alloy", Materials Engineering, p. 29, Oct. 1969.

Primary Examiner—Edward M. Coven
Assistant Examiner—Valerie Szczepanik
Attorney, Agent, or Firm—Hill, Van Santen, Steadman & Simpson

[57] ABSTRACT

A heart pacemaker system has an electrode line with a proximal end which is introduced into a connector of the pacemaker housing, and a distal end having an electrode head attachable to the heart of a user. One or more of the distal or proximal ends of the electrode line, the connector, or a region of the electrode line are provided with a component consisting of shape-memory metal. These components have a first shape at temperatures different from body temperature, and assume a second shape when at body temperature. The shape-memory metal component, if disposed at the proximal end of the electrode line or at the connector, is arrnaged to provide a firm mechanical and electrical connection of the electrode line with the pacemaker housing upon the change of shape of the component. The shape-memory metal component, if disposed at the distal end, is arranged to assist in providing, either directly or indirectly, a reliable, mechanical and electrical connection of the electrode line to the heart upon the change of shape of the component. The shape-memory metal component, if disposed in a region of the electrode line between the proximal and distal ends, assumes a first shape permitting easy introduction of the line through a vein, and a second shape after introduction, such as a curve.

13 Claims, 6 Drawing Sheets

HEART PACEMAKER SYSTEM WITH SHAPE-MEMORY METAL COMPONENTS

BACKGROUND OF THE INVENTION

1. Field of the Invention

The present invention is directed to a heart pacemaker system including a pacemaker housing with a connector portion, and an electrode line having a proximal end introduced into the connector portion, and a distal end having an electrode head attachable to the part of a user.

2. Description of the Prior Art

The goal of a heart pacemaker system is to produce a durable and reliable electrical connection between the pacemaker and the heart of a patient. Thus, a faultless mechanical and electrical connection between the connector portion of the pacemaker and the proximal end of the electrode line must be present. Moreover, the distal end of the electrode line must be anchored such that the electrode head can reliably transmit a stimulation pulse to the heart. The electrode line must also be shaped such that, in certain instances, portions of the electrode line and the electrode head lie against specific locations of the wall of the heart. The electrode head and the electrode line may also have a sensing function, so that heart activities can be sensed.

Threaded connections are frequently used for connecting the electrode line to the pacemaker housing. A pin plug of the electrode conductor is introduced into the pacemaker connector in the system disclosed in U.S. Pat. No. 4,226,244, and is secured therein with set screws. To prevent body fluid from penetrating into the connection, cover caps are subsequently introduced into the screw openings. A disadvantage of this system is the use of a plurality of parts in order to produce a connection. Moreover, the extremely small parts can easily be lost.

Fixing means are also necessary for attaching the electrode head at the distal end of the electrode line to the wall of the heart. Such an electrode line is disclosed in U.S. Pat. No. 3,939,843, wherein bristles bent backwardly are used as the fixing means. The bristles are bent and retained with a hold-down means at the insulation during introduction of the electrode line into a vein, so as to prevent damage to the wall of the vein. The hold-down means is retracted after the electrode head has been introduced, thereby releasing the bristles, which engage the trabeculae after the insertion. The electrode head is thus held at a desired location. The hold-down means is an additional part of the electrode line, thereby making the pacemaker electrode more expensive.

In electrode lines having traumatic fixing means, such as screws or wires, the electrode lines are often fashioned such that the fixing means are received in a hollow protective cylinder during the introduction process. The fixing means are displaceably seated such that a mandrin, guided inside the electrode line, forces the screw or wire out of the hollow cylinder after the electrode head has been introduced. Such a heart pacemaker electrode is disclosed in U.S. Pat. No. 4,280,512. If the mandrin has been incorrectly positioned during the introduction phase of the electrode to such a degree that the fixing means are entirely or partially exposed, damage to the vessel wall will result during introduction of the lead.

If an electrode line is to be introduced into the right atrium of the heart, it may be pre-formed into a J-shape as disclosed in German OS 25 06 694. In order to straighten the J-shaped section of the electrode line during introduction through a vein, a probe guide, which is somewhat thicker than a standard mandrin, is used. This makes the overall electrode line relatively stiff, which may cause difficulties during the introduction phase.

SUMMARY OF THE INVENTION

It is an object of the present invention to provide a heart pacemaker system wherein a simple and firm connection between the housing connector and the proximal electrode end is guaranteed, and wherein the electrode line together with the electrode head can be easily introduced into the heart and reliably anchored therein.

It is a further object of the present invention to provide a pre-formed electrode line which can be introduced without complications.

The above objects are achieved in accordance with the principles of the present invention in a heart pacemaker system wherein the electrode line is provided with at least one component consisting of a shape-memory metal alloy, the shape of the component changing in a predetermined manner given a temperature change. Such a metal alloy is described in detail in the advertising literature of Raychem Corporation of Menlo Park, California.

The shape-memory metal component may be disposed at the proximal end of the electrode line, for facilitating mechanical and electrical connection to the connector portion of the pacemaker housing, or may be disposed at the distal end of the electrode line for assuring reliable electrical connection to the heart, or the electrode line may have such components at both ends.

The metal components in the pacemaker system at both locations exhibit a defined initial shape at a first temperature, and a predetermined final shape, different from the initial shape, at a second temperature. The second temperature lies in the region of body temperature. The first temperature may be higher or lower than the second.

In one embodiment of the invention, the shape-memory metal component is disposed between parts of the heart pacemaker system which are to be electrically and/or mechanically firmly connected to each other. The shape of the metal component is selected such that a simple loose joining of the parts is possible at the first temperature, and the firm electrical and/or mechanical connection results after the change of shape occurring at the second temperature. For example, if the component is disposed at the proximal end of the electrode line, the physician simply has to plug the proximal electrode end loosely into the connector. After implantation into the patient, a good connection is quickly produced as the component assumes body temperature without additional parts. An extension line with a coupling member may be connected to the electrode line in this manner as well. If it is necessary for some purposes to provide a firm connection of this type for implantation, the parts may be electrically or otherwise heated, so as to roughly assume body temperature.

In one embodiment for use at the proximal end of the electrode line, the shape-memory metal component may have an annular shape at the first temperature, and assume an oval or angular shape at the second temperature. The shape-memory metal component may be attached either to the proximal electrode end in the connector, or in a coupling element if an extension line is to be used. As a result of a change of shape, the shape-memory metal component presses first against the electrode end and secondly against the inside walls of the connector or coupling piece.

In another embodiment, the shape-memory metal component may be arranged in the connector portion in the form of a spring, which lengthens at the second temperature so as to press against the proximal end of the electrode line.

In a further embodiment, the extended spring presses against the proximal end of the electrode line via an adaptor. Since it is the adaptor which is in direct contact with the proximal electrode end, the adaptor can be provided with any desired shape which is beneficial for making the desired connection, given the shape of the proximal end.

In another embodiment, the spring is disposed coaxially on the proximal end of the electrode line, and contracts axially but expands radially upon assuming the second temperature, thereby making the necessary electrical and mechanical connection.

For use at the distal end of the electrode line, the shape-memory metal component may be arranged so as to deform the electrical insulation which surrounds the electrode line in a desired manner. Thus the shape-memory component may be in the form of an annular ring which is initially at substantially the same diameter, beneath the insulation, as the electrical conductor within the electrode line. The annular shape-memory metal component may be received, for example, in an annular channel of the conductor. The electrode line is then introduced through a vein into the heart in the normal manner, with no danger of damage to the vessel wall. After insertion, the annular component will reach body temperature, and will expand outwardly, thereby deforming the insulation and causing the insulation to project outwardly, providing a fixing means for anchoring, for example, with the trabeculae, so that the electrode head is pressed firmly against the heart wall. The shape-memory metal component, upon reaching the second temperature, may assume an oval or angular shape, as desired.

It is also possible to make the shape-memory metal component a part of the electrode head itself, not covered by insulation.

In another embodiment for use at the distal end of the electrode line, the insulation may be provided with deformable bristles. The shape-memory metal component is disposed beneath the bristles. At the first temperature, the shape-memory metal component has substantially the same diameter as the exterior of the electrode line. Upon reaching the second temperature, however, the component will expand in diameter and push the bristles away from the electrode line, facilitating anchoring in the trabeculae.

In another embodiment, the shape-memory metal component itself may be in the form of bristles or prongs, disposed beneath the insulation, which lie against the inner conductor at the first temperature. Upon reaching the second temperature, the bristles or prongs will expand outwardly, thus deforming the insulation and providing an anchoring means at the distal end of the electrode line.

In embodiments wherein the fixing means are of the traumatic type, the fixing means may be arranged to be displaceable between two positions, being surrounded in one position by a hollow protective member, and projecting from the hollow member in the other position. The shape-memory metal component is disposed within the hollow member such that the change in shape which occurs upon a temperature change causes the component to displace the fixing means from one position to the other. Thus a probe guide or other separate instrument is not needed, as in conventional electrode lines.

In one embodiment of such a traumatic fixing means, the shape-memory metal component may be in the form of a spring disposed within the hollow member, which actuates a piston which in turn pushes the fixing element, such as a screw-in electrode, from within the hollow member to a position projection therefrom. In a further embodiment of this type of fixing means, the screw-in electrode itself may consist of shape-memory metal, and has a shape completely contained within the hollow member at the first temperature, and a shape projecting from the hollow member upon reaching the second temperature. This type of embodiment may be used for endocardial or myocardial attachment.

Lastly, in an embodiment designed to give the electrode line itself a pre-determined shape after implantation, a selected portion of the line, spaced from the distal end, may consist at least partially of shape-memory metal. The metal portion will have a straight shape at the first temperature, for easy insertion of the line through a vein, and upon reaching body temperature will assume a pre-determined different shape, such as a J-shape, and will deform the portion of the electrode line coextensive therewith to assume the shape.

DESCRIPTION OF THE PREFERRED EMBODIMENTS

Figure 1:
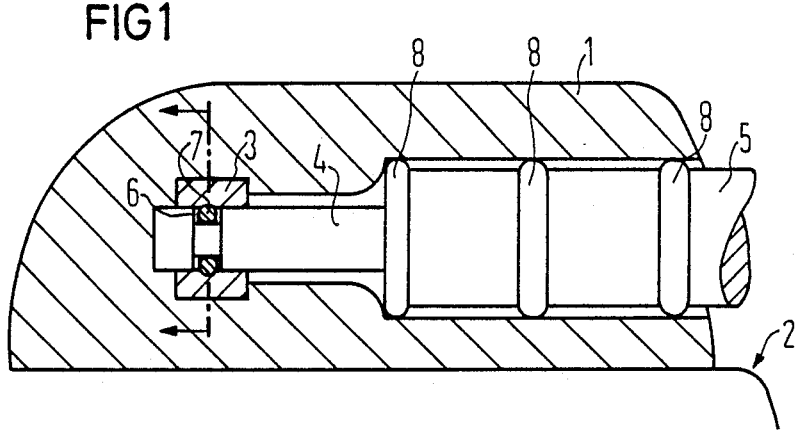
FIG. 1 is a side sectional view of the connector portion of a heart pacemaker system constructed in accordance with the principles of the present invention.

A portion of a heart pacemaker system constructed in accordance with the principles of the present invention as shown in FIG. 1. The portion includes a connector 1 of a pacemaker housing 2. The connector 1 includes a socket 3 into which the proximal electrode end 4 of an electrode line 5 is introduceable. The socket 3 serves to make an electrical connection between the components contained within the pacemaker housing 2 (the specific component connections not being shown) and the electrode line 5. The electrode end 4 has a channel 6 in which an annular component 7 consisting of shape-memory metal alloy is received.

Figure 2:
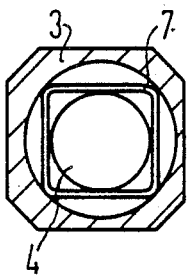
FIGS. 2, 3 and 4 are sectional views taken along the sectional line showing FIG. 1 of different shape-memory metal components assuming respectively different shapes.
Figure 3:
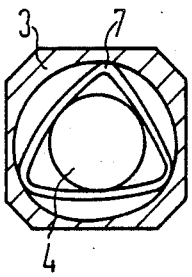
Figure 4:
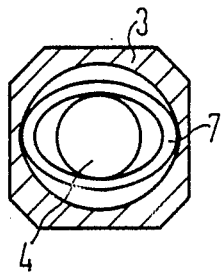

During pacemaker implantation, the electrode end 4 is first plugged into the connector 1 in a simple manner, so that the annular metal part 7 comes to lie within the socket 3. Due to friction between plastic seals 8 of the electrode line 5 and the connector 1, and the fit of the electrode end 4 against the socket 3, the electrode end 4 is temporarily mechanically and electrically connected to the pacemaker housing 2. After implantation the pacemaker housing 2 and the electrode end 4 are heated to body temperature. At this temperature, the annular metal part 7 assumes a different shape, such as the rectangular or square shape shown in FIG. 2 The metal part 7 is thereby pressed against the electrode end 4 and, at least the corners thereof, are pressed against the socket 3. A durable electrical connection and a firm mechanical connection between the pacemaker housing 2 and the electrode line 5 thereby arises. Such a connection may also be achieved, if desired, before implantation by heating the metal part 7 in a suitable manner. The annular metal part 7 may alternatively assume a triangular, oval or some other geometrical shape at body temperature, as shown in FIGS. 3 and 4. If the pacemaker housing 2 is removed from the body for replacement, and it is again permitted to assume a different temperature from body temperature, the metal part 7 will again assume its original annular shape, and the electrode line 5 can easily be separated from the connector 1.

Figure 5:
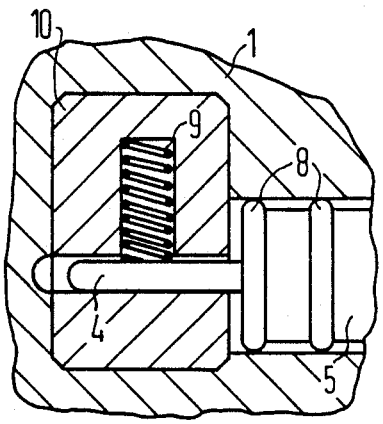
FIG. 5 is a side sectional view of a portion of the connector shown in FIG. 1 showing a further embodiment of the invention.

A further embodiment is shown in FIG. 5 wherein the shape-memory metal component is in the form of a spring which is received in a further socket 10. The spring-shaped metal component 9 lengthens at body temperature so as to press against the proximal electrode end 4, again producing a firm electrical and mechanical connection between the connector 1 and the electrode line 5.

Figure 6:
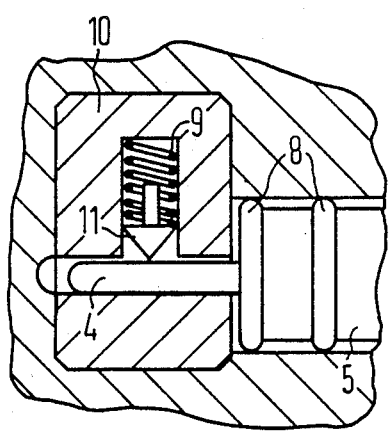
FIG. 6 is a side sectional view of the embodiment of FIG. 5 using an adaptor.

As shown in FIG. 6, a conically shaped adaptor 11 may be provided within the spring component 9, so that it is the adaptor 11 which presses against the electrode end 4.

Figure 7:
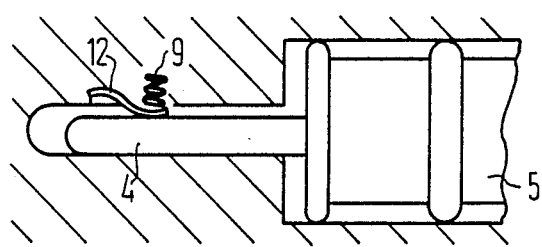
FIG. 7 is a side sectional view of a portion of the connector shown in FIG. 1 showing another embodiment of the invention.
Figure 8:
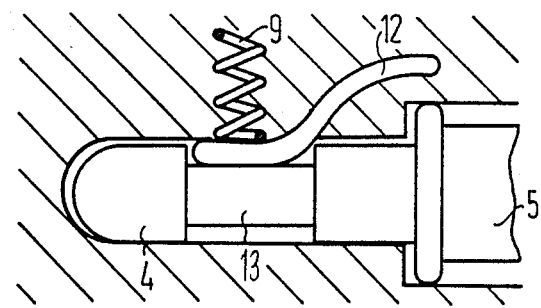
FIG. 8 is a side sectional view of the embodiment of FIG. 7 with a further modification.

In the embodiment of FIG. 7, a spring-shaped shape-memory metal component 9 is again used, however in this embodiment the adaptor 12 is tongue-shaped, with one end thereof being held within the connector 1, and the other end being disposed between the component 9 and the electrode end 4. In the embodiment of FIG. 8, the electrode end 4 is provided with an annular channel 13 in which the exposed end of the adaptor 12 is received.

Figure 9:
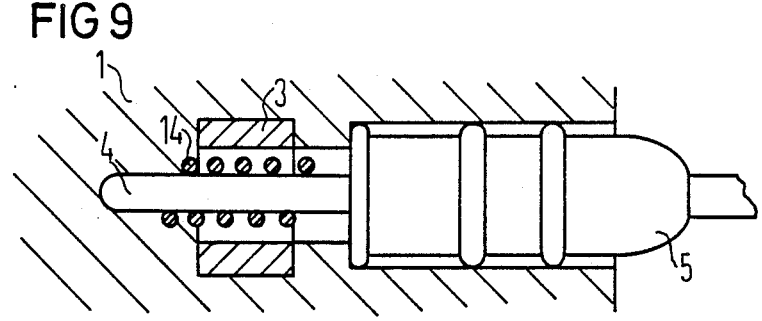
FIGS. 9 and 10 are side sectional views of a portion of the connector shown in FIG. 1 showing a further embodiment of the invention with the shape-memory metal component in its temperature dependent positions.
Figure 10:
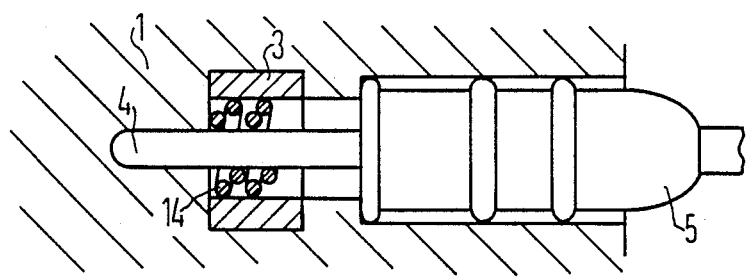

In the embodiment shown in FIGS. 9 and 10, the shape-memory metal component is again in the form of a spring 14, the spring 14 being coaxially aligned on the electrode end 4. The spring 14 is shown in the position corresponding to a first temperature in FIG. 9, and in a position corresponding to body temperature in FIG. 10, wherein the spring 14 is axially compressed but the diameter thereof has expanded to provide the necessary electrical and mechanical connections. The spring 14 may be attached to either the electrode end 4 or the socket 3.

Various embodiments for the distal end of the electrode line are shown in FIGS. 11 through 25.

Figure 11:
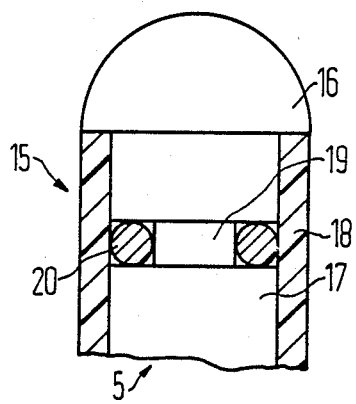
FIGS. 11 and 12 are side-sectional views of the distal end of an electrode line in a heart pacemaker system constructed in accordance with the principles of the present invention showing the shape-memory metal component in its temperature dependent positions.
Figure 12:
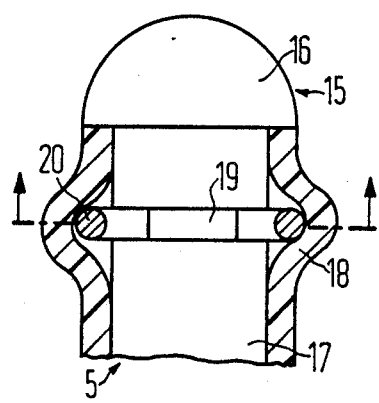
Figure 13:
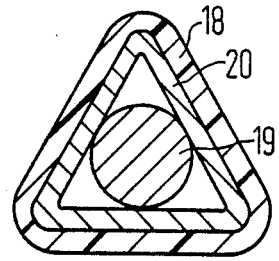
FIGS. 13, 14 and 15 are sectional views taken along the sectional line shown in FIG. 12 showing different shape-memory metal components assuming respectively different shapes.
Figure 14:
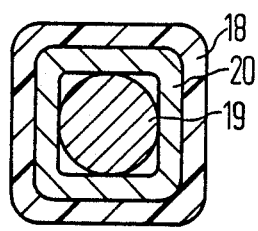
Figure 15:
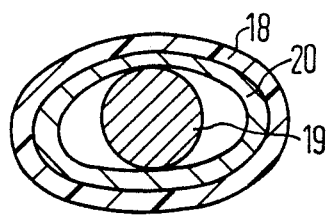

In FIG. 11, the distal end 15 of the electrode line 5 has an electrode head 16 which terminates an elongated electrical conductor 17, surrounded by electrical insulation 18. The distal end 15 includes a channel 19 in the conductor 17, in which an annular metal part 20 consisting of shape-memory metal is disposed. FIG. 11 shows the component 20 in the position it assumes at the first temperature, which does not distort the exterior of the electrode line 5 permitting easy introduction of the line through a vein. Upon reaching body temperature, the component 20 assumes the expanded shape shown in FIG. 12, thereby deforming a portion of the insulation 18 and providing fixing means for retaining the electrode head 16 against the wall of the heart. The component 20 may assume different shapes such as those shown in FIGS. 13 through 15, as desired.

Figure 16:
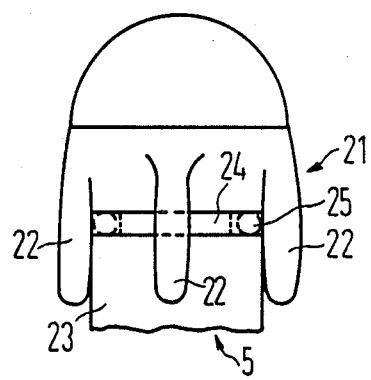
FIGS. 16 and 17 are side views of a further embodiment of a distal end of an electrode line constructed in accordance with the principles of the present invention showing the shape-memory metal component in its temperature dependent positions.
Figure 17:
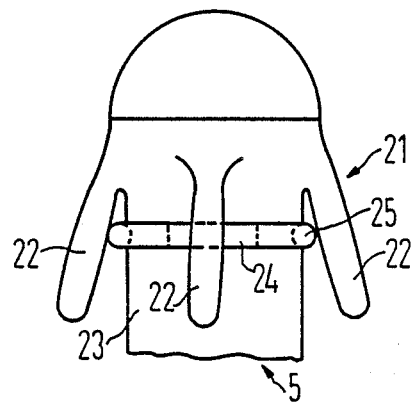

In a further embodiment shown in FIGS. 16 and 17, the distal end 21 of the electrode line 5 has a plurality of elongated bristles 22 which, in the position shown in FIG. 16, lie tightly against the insulation 23 at a temperature other than body temperature. The insulation 23 is provided with a channel 24 in which an annular component 25, consisting of shape-memory metal, is received. At body temperature, the component 25 expands forcing the bristles 22 away from the insulating 23 so as to project therefrom and provide a fixing means.

Figure 18:
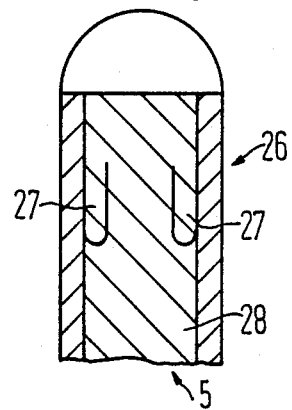
FIGS. 18 and 19 are sectional views of another embodiment of the distal end of a electrode line in a heart pacemaker system constructed in accordance with the principles of the present invention showing the shape-memory metal component in its temperature dependent positions.
Figure 19:
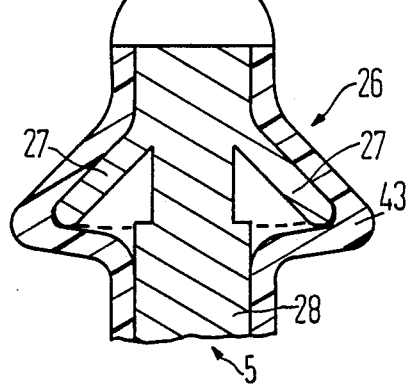

In the embodiment shown in FIGS. 18 and 19, the shape-memory metal components 27 are contained within the insulation at the distal end 26 of the electrode line 5, and at a temperature other than body temperature lie tightly against the conductor 28. Upon reaching body temperature, the components 27 assume the position as shown in FIG. 19, thereby deforming a portion 43 of the insulation and forming fin-like projections, again serving as fixing means.

It is also possible in each of the embodiments shown in FIGS. 11 through 15, 18 and 19 for the shape-memory metal components 20 and 27 to be exposed, rather than covered by insulation, so that the shape-memory metal components themselves form the fixing means.

Figure 20:
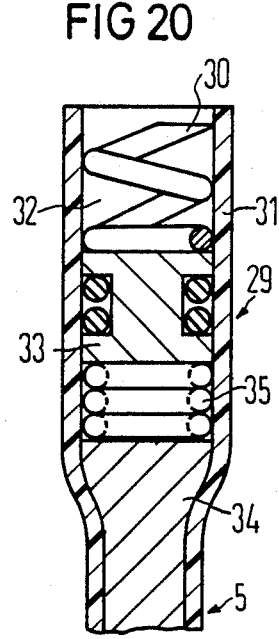
FIGS. 20 and 21 are side sectional views of the distal end of a traumatic attachment electrode line in a heart pacemaker system constructed in accordance with the principles of the present invention showing the shape-memory metal component in its temperature dependent positions.
Figure 21:
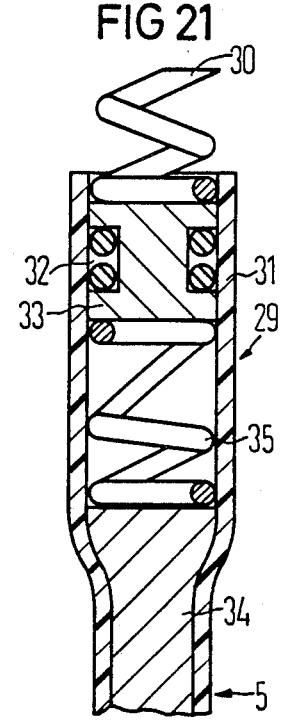

An embodiment showing a helical traumatic fixing means 30 serving as the electrode head is shown at the distal end 29 of an electrode line 5 as shown in FIG. 20. The fixing means 30 is surrounded by a hollow member 32 formed by the insulation 31. The fixing means 30 is secured to a piston 33 consisting of electrically conductive material. A component 35 consisting of shape-memory metal, in the form of a spring, is disposed between the electrical conductor 34 of the electrode line 5 and the piston 33. At a temperature other than body temperature, the component 35 is compressed as shown in FIG. 20. Upon reaching body temperature, the component 35 expands as shown in FIG. 21, thereby moving the piston 33 so as to force the fixing means 30 out of the hollow member 32 for attachment to the heart.

Figure 22:
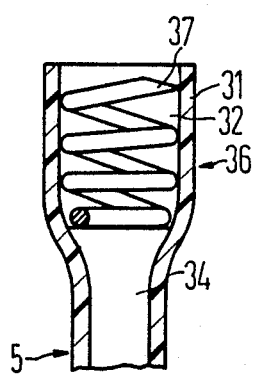
FIGS. 22 and 23 are side sectional views of a further embodiment of a traumatic attachment in an electrode line in a heart pacemaker system constructed in accordance with the principles of the present invention with the shape-memory metal component in its temperature dependent positions.
Figure 23:
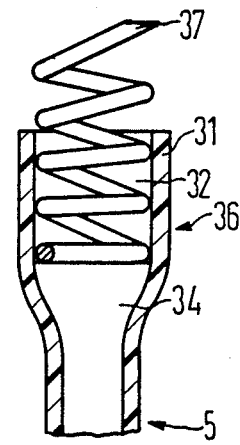

A further embodiment of a traumatic fixing means is shown in FIGS. 22 and 23 wherein the component 37, consisting of shape-memory metal, constitutes the fixing means. Again, a hollow member 32 is formed in the insulation 31 at the distal end 36 of the electrode line 5. The component 37 is received within the hollow member 32 at a temperature other than body temperature, and expands as shown in FIG. 23 upon reaching body temperature to project from the hollow member 32 for attachment to the heart.

Figure 24:
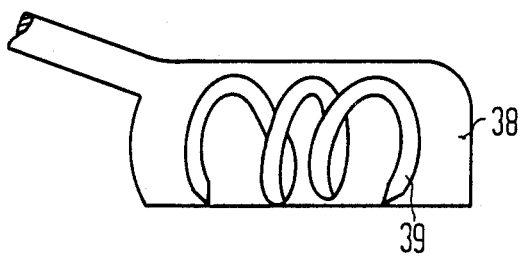
FIGS. 24 and 25 are side views of a myocardial attachment constructed in accordance with the principles of the present invention with the shape-memory metal component in its temperature dependent positions.
Figure 25:
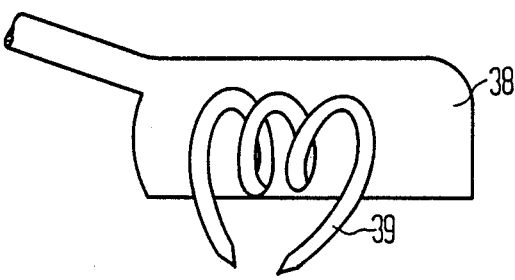

The distal end 38 of a myocardial attachment is shown in FIG. 24, wherein another spring-shaped component 39, consisting of shape-memory metal, is received in a chamber within the distal end 38. The component 39 assumes the position shown in FIG. 24 at a temperature other than body temperature, and assumes the position shown in FIG. 25, projecting from the distal end 38 for attachment to the heart, upon reaching body temperature.

Figure 26:
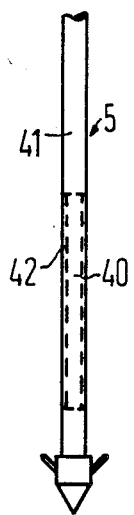
FIGS. 26 and 27 are side views of an electrode line constructed in accordance with the principles of the present invention with a shape-memory metal component in its temperature positions.
Figure 27:
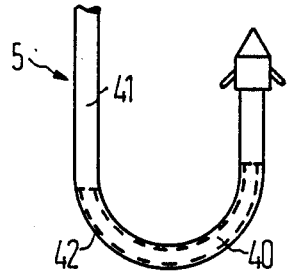

An electrode line 5 is shown in FIG. 26 having a conventional portion 41 and a deformable portion 40. The deformable portion 40 includes a component 42 consisting of shape-memory metal. The component 42, for example, may be in the form of a sleeve disposed between the electrical conductor and the insulation. At a temperature other than body temperature, the component 42 assumes the straight shape shown in FIG. 26 for easy introduction of the electrode line 5 through a vein. After implantation and upon reaching body temperature, the component 42, and thus the region 40, assume the curved or J-shape shown in FIG. 27.

Although modifications and changes may be suggested by those skilled in the art, it is the intention of the inventors to embody within the patent warranted hereon all changes and modifications as reasonably and properly come within the scope of their contribution to the art.

We claim as our invention:

1. A heart pacemaker system comprising:
    a pacemaker;
    an electrode line having a proximal end connected to said pacemaker and a distal end, said proximal and distal ends defining a longitudinal direction therebetween;
    fixing means disposed at said distal end of said electrode line for interacting with a wall of the heart of a patient to assist in retention of said distal end of said electrode line against said wall of the heart of a patient, said electrode line having an outer radial diameter adapted for permitting insertion of said electrode line through a vein of said patient; and
    a component consisting of shape-memory metal separate from but in contact with said fixing means which assumes a first shape at a first temperature which maintains said fixing means substantially at said outer radial diameter of said electrode line, and which assumes a second shape at a second temperature causing said fixing means at said distal end to project radially beyond said outer diameter, said second shape differing from said first shape only by being radially larger than said first shape.

2. A heart pacemaker system as claimed in claim 1 wherein said electrode line includes an electrical conductor surrounded by deformable electrical insulation, and wherein said component consisting of said shape-memory metal is disposed between said electrical conductor and said insulation.

3. A heart pacemaker system as claimed in claim 15 wherein said electrical conductor has a channel in which said component consisting of shape-memory metal is received.

4. A heart pacemaker system as claimed in claim 1 wherein said electrode line is covered with an electrically insulating sheath and wherein said fixing means further includes a plurality of bristles formed at said distal end as a part of said insulating sheath, and wherein said component consisting of shape-memory metal is disposed around said insulating sheath beneath said bristles such that said component in said first shape maintains said bristles against said sheath and in said second shape forces said bristles away from said sheath.

5. A heart pacemaker system as claimed in claim 1 wherein said first shape of said shape-memory metal is annular and said second shape is angular.

6. A heart pacemaker system as claimed in claim 1 wherein said first shape of said shape-memory metal is annular and wherein said second shape is oval.

7. A heart pacemaker system as claimed in claim 1 wherein said electrode line has an electrical conductor, and wherein said component consisting of shape-memory metal consists of at least one prong, and herein said component in said first shape is disposed against said electrical conductor, and wherein said component in said second shape projects away from said electrical conductor.

8. A heart pacemaker system comprising:
    a pacemaker;
    an electrode line having a proximal end connected to said pacemaker and a distal end; and traumatic fixing means disposed at said distal end of said electrode line for assisting in retention of said distal end of said electrode line against a wall of the heart of a patient, said fixing means including a hollow member having an open end, and a helical electrode, a piston and a component consisting of shape-memory metal disposed in said hollow member with said helical electrode closest to said open end and said piston between said helical electrode and said component consisting of shape-memory metal, said component consisting of shape-memory metal assuming a first shape at a first temperature which maintains said helical electrode within said hollow member, and assuming a second shape at a second temperature which moves said piston within said hollow member and forces said helical electrode out of said open end of said hollow member so as to at least partially project therefrom.

9. A heart pacemaker system comprising:
a pacemaker;
an electrode line having a proximal end connected to said pacemaker and a distal end; and
fixing means disposed at said distal end of said electrode line for assisting in retaining said distal end of said electrode line against a wall of the heart of a patient, said fixing means including a hollow member having an open end, and a helical component consisting of shape-memory metal disposed within said hollow member, said helical component assuming a first shape at a first temperature which is fully contained within said hollow member, and assuming a second shape at a second temperature which at least partially projects from said open end of said hollow member.

10. A heart pacemaker system comprising:
a pacemaker;
an electrode line having a proximal end connected to said pacemaker and a distal end; and
fixing means disposed at said distal end of said electrode line for assisting in attachment of said distal end of said electrode line to the myocardium of the heart of a patient, said fixing means including a hollow chamber and a helical component consisting of shape-memory metal and having opposite ends each adapted to penetrate the myocardium, said helical component assuming a first shape at a first temperature which is fully contained within said chamber, and a second shape at a second temperature with both of said ends projecting from said chamber.

11. A heart pacemaker system comprising:
an electrode line having a proximal end and a distal end;
a pacemaker having a connector means for attaching said proximal end of said electrode line to said pacemaker, said connector means and said proximal end of said electrode lines including respective elements which are capable of being electrically and mechanically connected; and
a component consisting of shape-memory metal disposed between said elements of said connector and said proximal end, said component consisting of shape-memory metal assuming an annular shape at a first temperature to loosely connect said elements and assuming an oval shape at a second temperature to rigidly connect said elements.

12. A heart pacemaker system comprising:
an electrode line having a proximal end and a distal end;
a pacemaker having a connector means for attaching said proximal end of said electrode line to said pacemaker, said connector means and said proximal end of said electrode lines including respective elements which are capable of being electrically and mechanically connected; and
a component consisting of shape-memory metal disposed between said elements of said connector and said proximal end, said component consisting of shape-memory metal assuming an annular shape at a first temperature to loosely connect said elements and assuming an angular shape at a second temperature to rigidly connect said elements.

13. A heart pacemaker system comprising:
an electrode line having a proximal end and a distal end;
a pacemaker having a connector means for attaching said proximal end of said electrode line to said pacemaker, said connector means and said proximal end of said electrode line including respective elements which are capable of being electrically and mechanically connected; and
a spring consisting of shape-memory metal disposed between said elements of said connector and said proximal end, said spring assuming a first diameter at a first temperature to loosely connect said elements and assuming a second diameter, larger than said first diameter, at a second temperature to rigidly connect said elements.

* * * * *